United States Patent [19]
Wood et al.

[11] Patent Number: 6,037,468
[45] Date of Patent: Mar. 14, 2000

[54] GLYCOSYLATED INDOLOCARBAZOLE SYNTHESIS

[75] Inventors: John L. Wood, Hamden, Conn.; Brian M. Stoltz, Cambridge, Mass.

[73] Assignee: Yale University, New Haven, Conn.

[21] Appl. No.: 09/206,082

[22] Filed: Dec. 4, 1998

Related U.S. Application Data

[63] Continuation-in-part of application No. 08/817,230, filed as application No. PCT/IB96/00987, Aug. 9, 1996, abandoned.
[60] Provisional application No. 60/002,164, Aug. 11, 1995.
[51] Int. Cl.$^7$ .................................................. C07D 498/22
[52] U.S. Cl. ........................................................... 540/545
[58] Field of Search ............................................... 540/545

[56] References Cited

FOREIGN PATENT DOCUMENTS 05247054  9/1993  Japan .

OTHER PUBLICATIONS

Fredenhagen, A., & Peter, H.H., Tetrahedron 52:1235–1238 (1996).
Link, J.T., et al., J. Am. Chem. Soc. 115:3782–3783 (1993).
Omura, S., S.W., et al., J. Antibiotics 48:535–548 (1995).
McCombie, S.W., et al., Bioorg. Med. Chem. Lett. 3:1537–1542 (1993).
Pirrung, M.C., et al., J. Org. Chem. 60:2112–2124 (1995).
Stoltz, B.M., & Wood, J.L., Tetrahedron Lett. 36:8543–8544, No. 47 (Nov. 20, 1995).
Stoltz, B.M., & Wood, J.L., Tetrahedron Lett. 37:3929–3930, No. 23 (Jun. 3, 1996).
Wood, J.L., et al., J. Amer. Chem. Soc. 117:10413–10414 (1995).
Wood, J.L., et al., J. Amer. Chem. Soc. 118:10656–10657, No. 43 (and supplementary materials (Oct. 30, 1996).
Wood, J.L., et al., Tetrahedron Lett. 37:7335–7337, No. 41 (and supplementary materials) Oct. 7, 1996.

*Primary Examiner*—Laura L. Stockton
*Attorney, Agent, or Firm*—Mary M. Krinsky

[57] ABSTRACT

Tertiary alcohols containing the structural features illustrated in 3 or 4 below (Scheme I) are prepared by reacting at least one diazo carbonyl compound, e.g., 1 in Scheme I) and at least one allylic alcohol (e.g., 2 in Scheme I) in a coupling reaction run under conditions that produce carbene or carbenoid intemediates from the diazo containing substrate such as transition metal catalysis or either thermal or photochemical decomposition. In some preferred embodiments, Rh$_2$(OAc)$_4$ is employed to catalyze the coupling reaction.

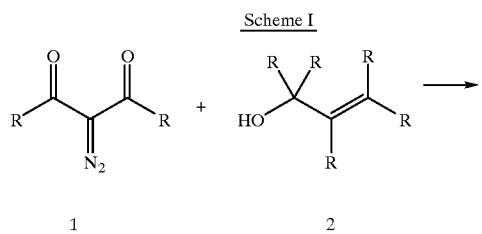

Scheme I

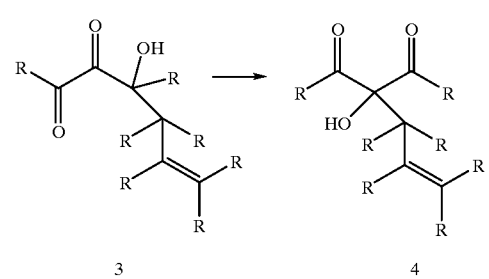

Wherein R represents a substituent comprised of any number and combination of the elements H, C, N, S, Si, O, Cl; Br, I, and F Indolocarbazoles (e.g., 7 below) are prepared by coupling of diazo carbonyl compounds (e.g., 5) and biindoles (e.g., 6). Indolocarbazoles are furanosylated (e.g., 7) with acetals (e.g., 8) or their open chain congeners (e.g., 9) under conditions known to promote acetal exchange or formation, such as protic or Lewis acids. Furanosylated indolocarbazoles (e.g., 10) are also prepared via ring contraction of pyranosylated indolocarbazoles (e.g., 11) under conditions know to effect oxidation and benzylic acid type rearrangements, and pyranosylated indolocarbazoles (e.g., 11) are prepared via ring expansion of the furanosylated congeners (e.g., 10).

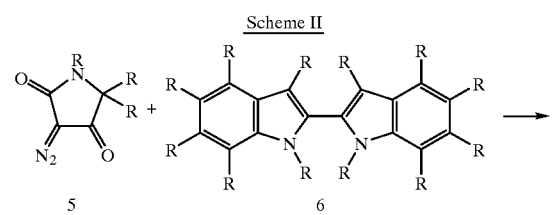

Scheme II

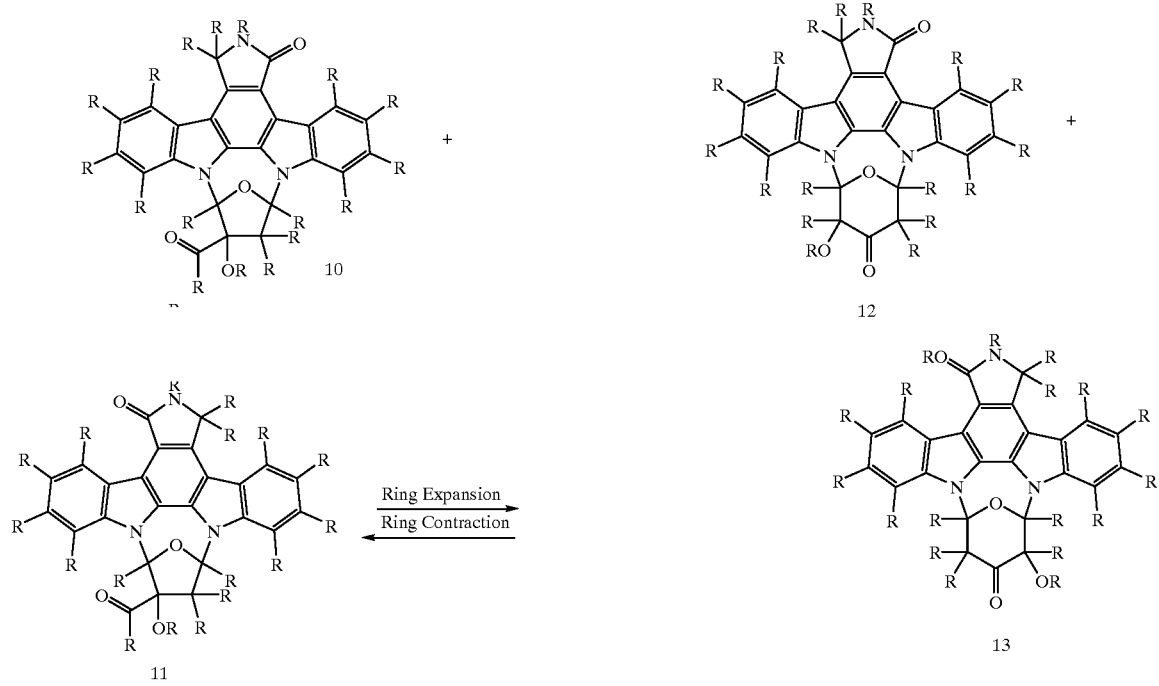
22 Claims, No Drawings

GLYCOSYLATED INDOLOCARBAZOLE SYNTHESIS

RELATED APPLICATION DATA

This application is a continuation-in-part of co-pending U.S. application Ser. No. 08/817,230, filed Jun. 4, 1997 now abandoned as the U.S. national phase entry under 35 U.S.C. 371 of PCT/IB96/00987, which had an international filing date of Aug. 9, 1996, claiming benefit of U.S. application Ser. No. 60/002,164 filed Aug. 11, 1995, all of which are incorporated herein in their entireties by reference.

TECHNICAL FIELD OF THE INVENTION

This invention relates to the synthesis of tertiary alcohols by coupling of diazo carbonyl compounds with allylic alcohols under conditions that produce carbene or carbenoid intermediates. Both furanosylated and pyranosylated indolocarbazoles are prepared, including naturally occurring compounds as well as a range of structurally diverse analogues.

BACKGROUND OF THE INVENTION

Originally discovered in the course of screening for microbial alkaloids, staurosporine and structurally related compounds have been the object of considerable investigation for various biomedical purposes for the past twenty years (for a review, see Omura, et al.). It has been recently reported that staurosporine and its derivatives, for example, inhibit smooth muscle contraction, platelet aggregation, neurotrophic activity, and, most importantly, protein kinases in vitro and in vivo (ibid.).

Disruption of cellular signal transduction via kinase malfunction has been related to the onset of several disease states, including rhematoid arthritis, systemic lupus erythematosis, diabetes metillus and Alzheimer's disease. For example, the clinical severity of Alzheimer's disease correlates well with the formation of amyloid plaques and neurofibrillary tangles; both manifest paired helical filaments (PHF) that possess an overphosphorylated microtubule associated protein (M.A.P., also known as $\tau$-protein). It has been suggested that overphosphorylation may lead to conformational changes that inhibit $\tau$ binding to microtubules. Recently, a bovine $\tau$-kinase denominated PK40 (molecular weight 40,000) has been isolated and shown to induce a gel mobility shift of PHF-$\tau$. PK40 is not closely associated with the cytoskeleton and appears to be a member of the extracellular regulated kinases. Specific inhibition of enzymes like PK40 by small, orally bioavailable compounds, promise to be a highly successful means of treating Alzheimer's disease.

Unfortunately, the structural homology shared by the many kinase isozymes has impeded the development of selective and therapeutically useful inhibitors. It would be desirable to have others.

SUMMARY OF THE INVENTION

It is a specific objective of the invention to provide a synthesis for (+)- and (−)-K252a, analogues of K252a, staurosporine and its congeners, (+)-RK286c and (−)-RK286c, (+)-MLR52 and (−)-MLR52, (+)-TAN 1030a and (−)-TAN 1030a, (+)-UNC-01 and (−)-UNC-01, (+)-RK1409 and (−)-RK1409, and the like.

It is another and more general object of the invention to provide for the synthesis of furanosylated and pyranosylated indolocarbzoles, particularly the interconversion of furanosylated indolocarbazoles to the corresponding pyranosylated derivatives.

It is a further objective of the invention to provide an efficient approach to the synthesis of enantioenriched tertiary alcohols.

These and other objectives are accomplished by the present invention, which provides a process for the preparation of tertiary alcohols containing the structural features illustrated in 3 or 4 below (Scheme I). The process utilizes at least one carbonyl compound, e.g., 1 in Scheme I) and at least one allylic alcohol (e.g., 2 in Scheme I) in a coupling reaction that is run under conditions that produce carbene or carbenoid intermediates from the diazo-containing substrate. These conditions include transition metal catalysis or either thermal or photochemical decomposition. In some preferred embodiments illustrated hereafter, $Rh_2(OAc)_4$ is employed to catalyze the coupling reaction.

Scheme I

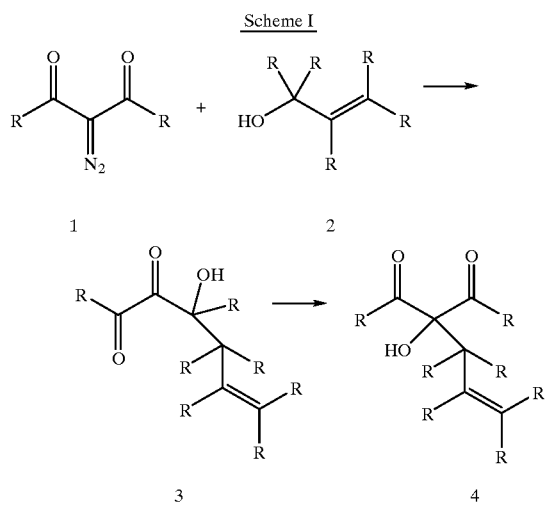

Wherein R represents a substituent comprised of any number and combination of the elements H, C, N, S, Si, O, Cl; Br, I, and F As used herein, terminology referring to R as representing a substituent comprised of any number and combination of the elements H, C, N, S, Si, O, Cl, Br, I and F refers, as is known to those skilled in the art, to alkyl, alkenyl, alkynyl, aryl, cyclic or heterocyclic substituents comprised of these elements that may be alkaloid substituents. The definition encompasses the following R groups:

a) a $C_{3-10}$ branched or unbranched alkyl, alkenyl, or alkynyl, which may be partially or fully silylated or halogenated, or combinations thereof, and optionally substituted by one to three substituents consisting of aryl or heteroaryl, wherein the aryl or heteroaryl rings may be optionally substituted with one to five groups consisting of either $C_{1-6}$ branched or unbranched alkyl, which may be partially or fully halogenated, $C_{3-8}$ cycloalkyl, halo, hydroxy, cyano, $C_{1-3}$ alkyloxy, which may be partially or fully halogenated, nitro, amino, alkylamino, dialkylamino, carbonylamine, carbonyldialkylamine, carboxy, carbonyloxy $C_{1-4}$ branched or unbranched alkyl;

b) a $C_{3-10}$ branched or unbranched cycloalkyl which may be partially or fully silylated or halogenated, or combinations thereof, and optionally substituted by one to three substituents consisting of aryl or heteroaryl, wherein the aryl or heteroaryl rings may be optionally substituted with one to five groups consisting of either $C_{1-6}$ branched or unbranched alkyl, which may be partially or fully halogenated, $C_{3-8}$ cycloalkyl, halo, hydroxy, cyano, $C_{1-3}$ alkyloxy, which may be partially or fully halogenated, nitro, amino, alkylamino, dialkylamino, carbonylamine, carbonyldialkylamine, carboxy, carbonyloxy $C_{1-4}$ branched or unbranched alkyl;

c) a $C_{5-8}$ branched or unbranched cycloalkenyl which may be partially or fully silylated or halogenated, or combinations thereof, and optionally substituted by one to three substituents consisting of aryl or heteroaryl, wherein the aryl or heteroaryl rings may be optionally substituted with one to five groups consisting of either $C_{1-6}$ branched or unbranched alkyl, which may be partially or fully halogenated, $C_{3-8}$ cycloalkyl, halo, hydroxy, cyano, $C_{1-3}$ alkyloxy, which may be partially or fully halogenated, nitro, amino, alkylamino, dialkylamino, carbonylamine, carbonyldialkylamine, carboxy, carbonyloxy $C_{1-4}$ branched or unbranched alkyl;

d) an aryl or heteroaryl optionally substituted with one to five groups consisting of either aryl, heteroaryl, $C_{1-6}$ branched or unbranched alkyl, which may be partially or fully silylated or halogenated, $C_{3-8}$ cycloalkyl, $C_{1-5}$ alkylaryl, halo, hydroxy, cyano, $C_{1-3}$ alkyloxy, which may be partially or fully halogenated, aryloxy, heteroaryloxy, nitro, amino, alkylamino, dialkylamino, arylamino, heteroarylamino, carbonylamine, carbonyldialkylamine, carboxy, carbonyloxy $C_{1-4}$ branched or unbranched alkyl, $C_{1-5}$ alkylcarbonyl $C_{1-4}$ branched or unbranched alkyl, $C_{1-5}$ alkyl or alkenylcarboxy, $C_{1-5}$ alkylamine, $C_{1-5}$ alkyldialkylamine, $C_{1-5}$ alkylthio, $C_{1-5}$ alkylsulfinyl, $C_{1-5}$ alkylsulfonyl, sulfonylamine, sulfonyldialkylamine;

(e) carboxy, carbonyloxy $C_{1-4}$ branched or unbranched alkyl, $C_{1-5}$ alkylcarbonyl $C_{1-4}$ branched or unbranched alkyl, $C_{1-5}$ alkyl or alkenylcarboxy, aryloxy, heteroaryloxy, nitro, amino, alkylamino, dialkylamino, arylamino, heteroarylamino, carbonylamine, carbonyldialkylamine $C_{1-5}$ alkylamine, $C_{1-5}$ alkyldialkylamine, $C_{1-5}$ alkylthio, $C_{1-5}$ alkylsulfinyl, $C_{1-5}$ alkylsulfonyl, sulfonylamine, sulfonyldialkylamine, and partially and fully halogenated or silylated derivatives thereof;

(f) a hydrogen;

(g) a halogen;

(h) a silyl group; and (i) mixtures of any of these.

Embodiments wherein R is H, an alkyl or an aryl are particularly preferred. In many embodiments, the R is an H or a lower unsubstituted alkyl group. As used herein, indicated above, and illustrated below, when discussing substitutent R groups, the "or" indicates R groups comprising H, alkyl, or aryl groups, or mixtures of any of these. For example, the latter-mentioned subgroup encompasses alkaloids bearing only H, only alkyl groups, and mixtures thereof. Illustrative R groups in the examples that follow are H, Me, t-Bu, 3,4-DMB, and PMB.

The invention more specifically provides a process for the construction of indolocarbazoles (e.g., 7 below) from the coupling of diazo carbonyl compounds (e.g., 5) and biindoles (e.g., 6). The invention also provides a process for the stereoselective preparation of glycosylated indolocarbazoles like but not limited to 10 and 11 via ftiranosylation of indolocarbozoles (e.g., 7) with acetals (e.g., 8) or their open chain congeners (e.g., 9) under conditions known to promote acetal exchange or formation, such as protic or Lewis acids.

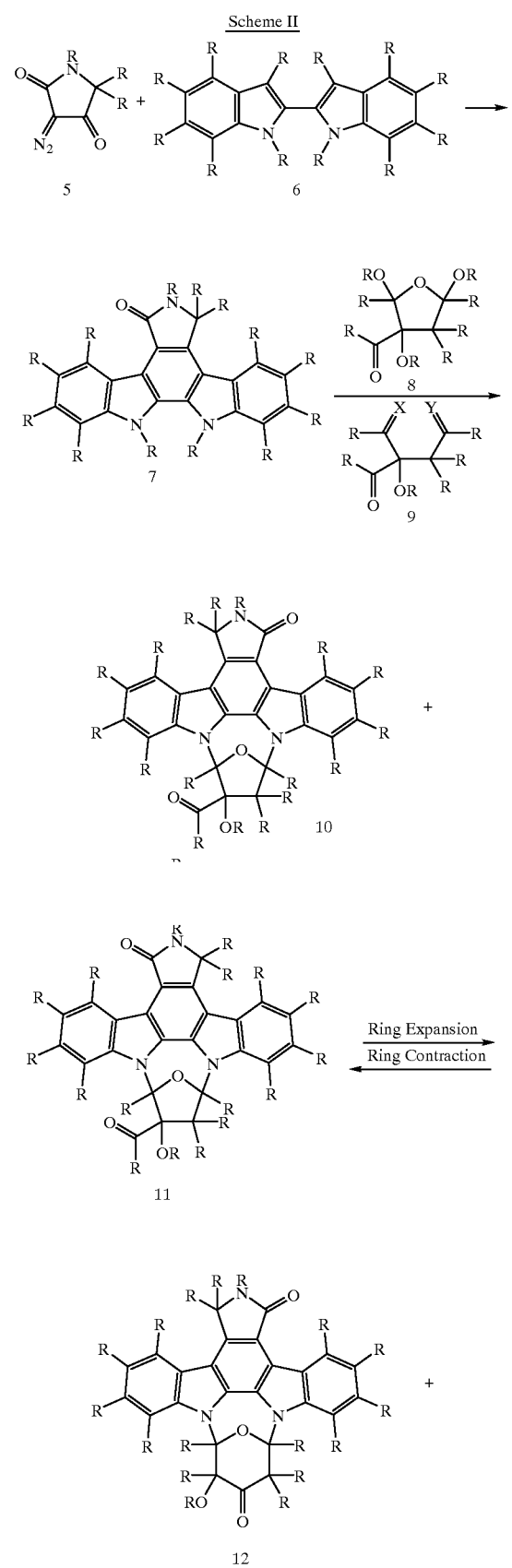

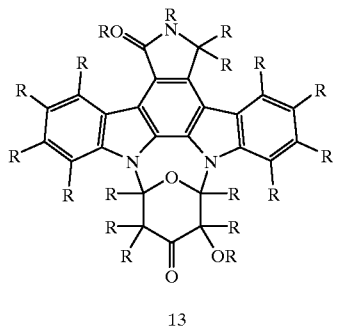

13

As illustrated in Scheme II above, processes of the invention also provide furanosylated indolocarbazoles (e.g., 10) via ring contraction of pyranosylated indolocarbazoles (e.g., 12) under conditions known to effect oxidation and benzylic acid type rearrangements. The invention correspondingly provides processes for the construction of pyranosylated indolocarbazoles (e.g., 12) via ring expansion of the furanosylated congeners (e.g., 10).

DETAILED DESCRIPTION OF THE INVENTION

This invention is based upon several new processes that when combined in-total or in-part can lead to the enantioselective syntheses of various indolocarbazoles.

Unless expressly noted to the contrary, the following definitions apply:

The term "alkyl" refers to a saturated aliphatic radical containing from one to ten carbon atoms. "Alkyl" refers to both branched and unbranched alkyl groups. Preferred alkyl groups are straight-chain alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms. "Alkyl", as used herein, includes unsubstituted alkyl radicals, those radicals that are partially or fully halogenated and those radicals substituted with one to four, preferably one or two, substituents selected from amino, cyano, nitro, methoxy, ethoxy and hydroxy. The term "cycloalkyl" refers to the cyclic analog of an alkyl group, as defined above. Preferred cycloalkyl groups are saturated cycloalkyl groups containing from three to eight carbon atoms, and more preferably, three to six carbon atoms. "Alkyl" and "cycloalkyl", as used herein, include unsubstituted alkyl and cycloalkyl radicals, those radicals that are partially or fully halogenated and those radicals substituted with one to four, preferably one or two, substituents selected from halo, amino, cyano, nitro, methoxy, ethoxy and hydroxy. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom.

The terms "alkenyl" and "alkynyl" refer to mono- or polyunsaturated aliphatic hydrocarbon radical containing from two to twelve carbon atoms, containing at least one double or triple bond, respectively. "Alkenyl" and "alkynyl" refer to both branched and unbranched alkenyl and alkynyl groups. Preferred alkenyl and alkynyl groups are straight chain alkenyl or alkynyl groups containing from two to eight carbon atoms and branched alkenyl or alkynyl groups containing from five to ten carbon atoms. More preferred alkenyl and alkynyl groups are straight chain alkenyl or alkynyl groups containing from two to six carbon atoms and branched alkenyl or alkynyl groups containing from five to eight carbon atoms. The term "cycloalkenyl" refers to the cyclic analog of an alkenyl group, as defined above. Preferred cycloalkenyls include cycloalkenyl rings containing from three to eight carbon atoms, and more preferably, from three to six carbon atoms. "Alkenyl", "alkynyl" and "cycloalkenyl", as used herein, include unsubstituted alkenyl or alkynyl radicals, those radicals that are partially or fully halogenated and those radicals substituted with one to four, preferably one or two, substituents selected from halo, amino, cyano, nitro, methoxy, ethoxy and hydroxy.

The term "aryl" refers to an aromatic carbocyclic radical having from 5 to 8 carbon atoms if monocyclic and from 8 to 12 carbon atoms if bicyclic. Preferred aryl radicals include pheniyl and naphthyl. The term "heteroaryl" refers to any aryl radical in which one or more carbon atoms are replaced with a heteroatom. The terms "aryl" and "heteroaryl" also refer to partially or fully halogenated aryl and heteroaryl groups substituted with halo, alkyl; hydroxyl; nitro; —COOH; —CO(lower alkoxy); CO(lower alkyl); amino; alkylamino; dialkylamino; alkoxy; —NCOH; —NCO(lower alkyl); —NSO$_2$-Ph(halo)$_{0-3}$, Ph; —O-Ph; naphthyl; —O-naphthyl; pyrrolyl; pyrrolyl substituted with lower alkyl; pyridyl; pyridinyl; pyrazinyl; pyrimidinyl and pyridazinyl.

As summarized above, in a practice of the invention at least one diazo carbonyl compound and at least one allylic alcohol of structures 1 and 2, respectively (Scheme III), are combined to produce tertiary alcohols of structures 3 and/or 4 in Scheme III. A preferred embodiment employs but is not limited to the use of transition metal catalysts in the form of ligated Rh(II) complexes, for example Rh$_2$(OAc)$_4$, to produce 3 and a Lewis acid like but not limited to BF$_3$.Et$_2$O to convert 3 to 4. In alternative imbodiments the decomposition of the diazo substrate to the corresponding carbene or carbenoid involves catalysis by complexes of: Cu(II), Mn(II), Fe(II), Co(II), Ni(O), Ni(II), Zn(II), Mo(II), Ru(II), Ru(III), Bronsted and Lewis acids, thermolysis, and/or photolysis. The derived tertiary alcohols of structure 4 are further manipulated by standard chemical procedures to produce acetals of structure 8 and the corresponding open chain congeners of structure 9. The later are utilized in the furanosylation process and total syntheses described below.

Scheme III

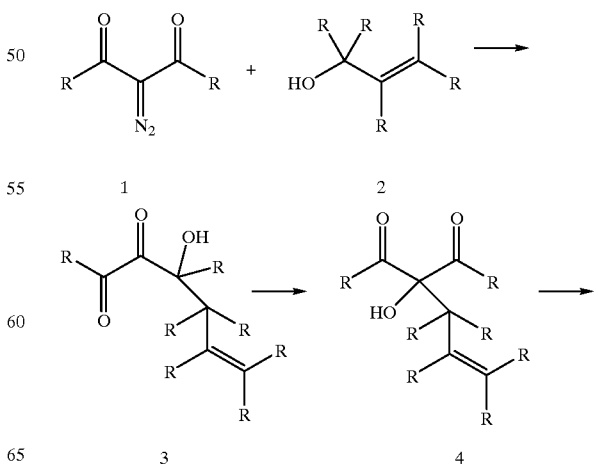

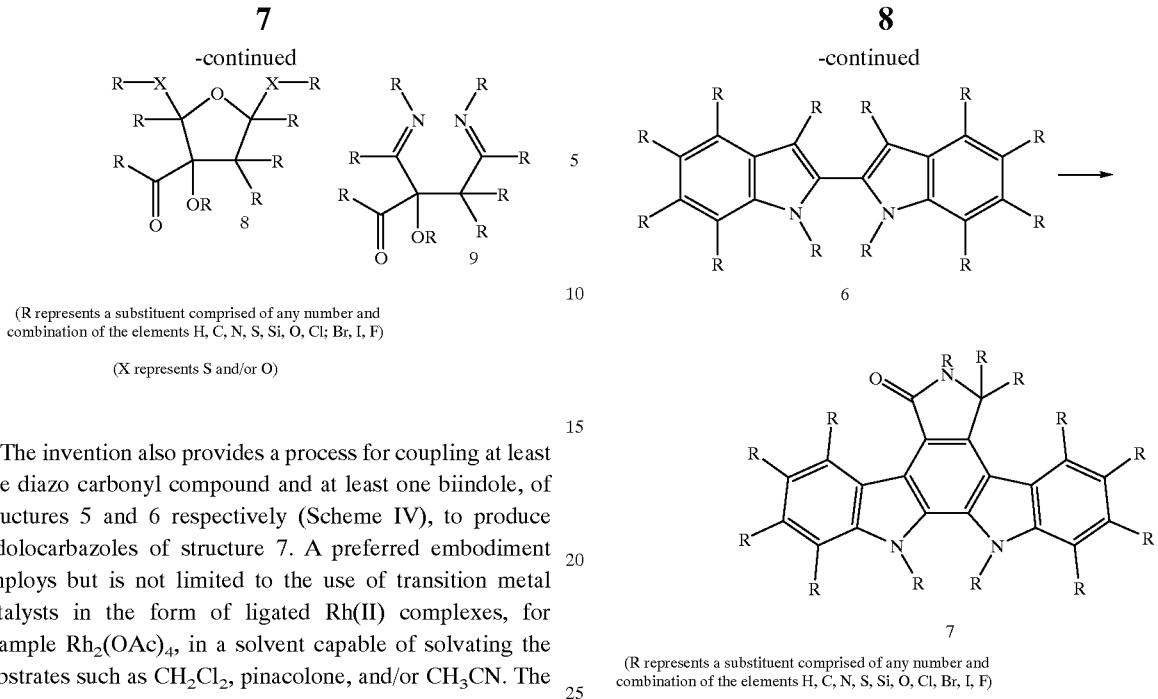

(R represents a substituent comprised of any number and combination of the elements H, C, N, S, Si, O, Cl; Br, I, F)

(X represents S and/or O)

The invention also provides a process for coupling at least one diazo carbonyl compound and at least one biindole, of structures 5 and 6 respectively (Scheme IV), to produce indolocarbazoles of structure 7. A preferred embodiment employs but is not limited to the use of transition metal catalysts in the form of ligated Rh(II) complexes, for example $Rh_2(OAc)_4$, in a solvent capable of solvating the substrates such as $CH_2Cl_2$, pinacolone, and/or $CH_3CN$. The reaction is carried out under conditions such that products are formed at a convenient rate such as for example about 20–30 minutes at reflux. In alternative embodiments initiating the process via decomposition of the diazo substrate to the corresponding carbene or carbenoid involves catalysis by complexes of: Cu(II), Mn(II), Fe(II), Co(II), Ni(O), Ni(II), Zn(II), Mo(II), Ru(II), Ru(III), Bronsted and Lewis acids, thermolysis, and/or photolysis.

(R represents a substituent comprised of any number and combination of the elements H, C, N, S, Si, O, Cl, Br, I, F)

The invention also provides a process for the stereoselective furanosylation of indolocarbazoles of a structure 10 or 11 with acetals and/or their open chain congeners, of structures 8 and 9 respectively in Scheme V, under conditions that promote acetal exchange or formation, such as but not limited to Bronsted or Lewis acids such as camphor sulfonic acid (CSA), para-toluene sulfonic acid (PTSA), or $BF_3.Et_2O$ (McCombie et al.). A preferred embodiment employs but is not limited to the use of camphor sulfonic acid (CSA) as the catalyst and the dichloroethane as the solvent in a coupling reaction that stereoselectively produces the regioisomeric furanosylated indolocarbazoles 10 and 11 in about 80% yield. The derived indolocarbazoles of structure 10 are manipulated by standard chemical procedures to produce 14 (K252a).

Scheme IV

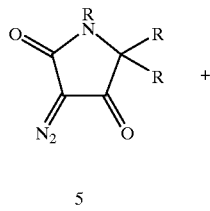

Scheme V

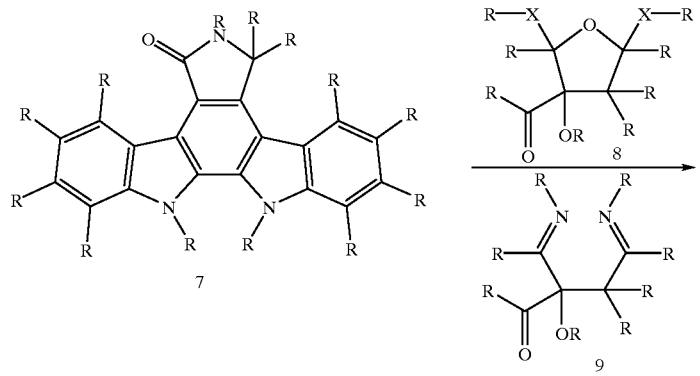

-continued

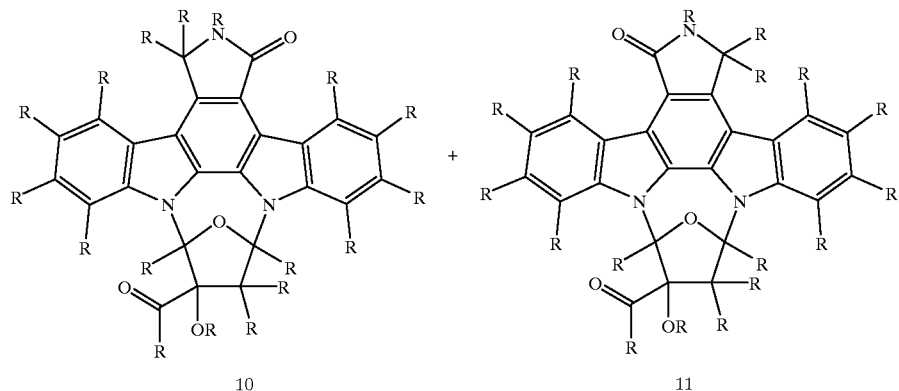

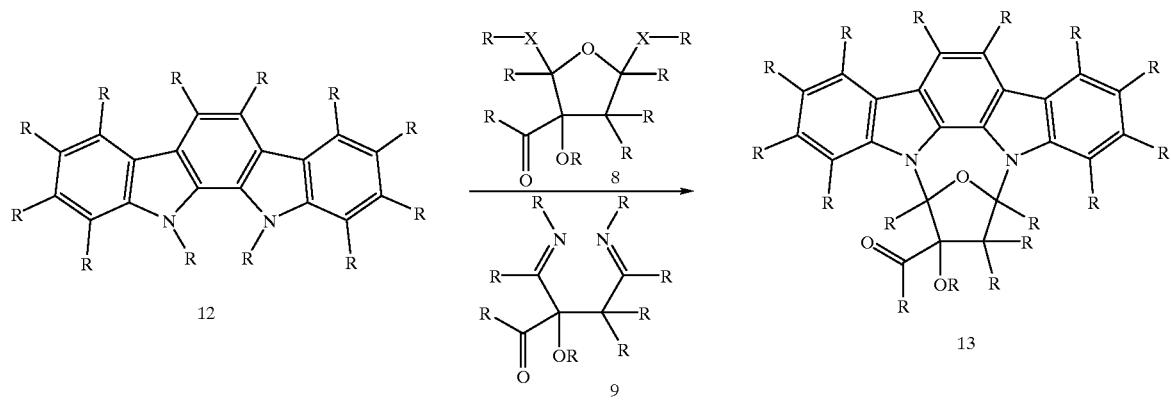

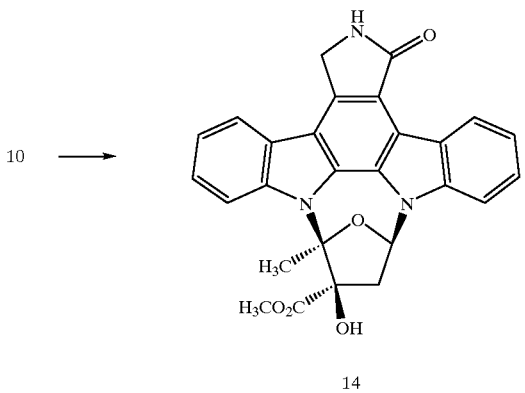

(R represents a substituent comprised of any number and combination of the elements H, C, N, S, Si, O, Cl, Br, I, F)

(X represents S and/or O)

As illustrated in Scheme VI, the invention also provides a process for the ring contraction of pyranosylated indolocarbazoles of structure 15 and/or 16 to furanosylated indolocarbazoles of structure 10 and/or 11 under conditions that in single- or two-step fashion can effect oxidation and benzylic acid type rearrangement (Fredenhagen et al.). A preferred embodiment employs but is not limited to a single-step procedure wherein CuCl is used as both the oxidant and rearrangement promoter and methanol is used as the solvent.

Scheme VI

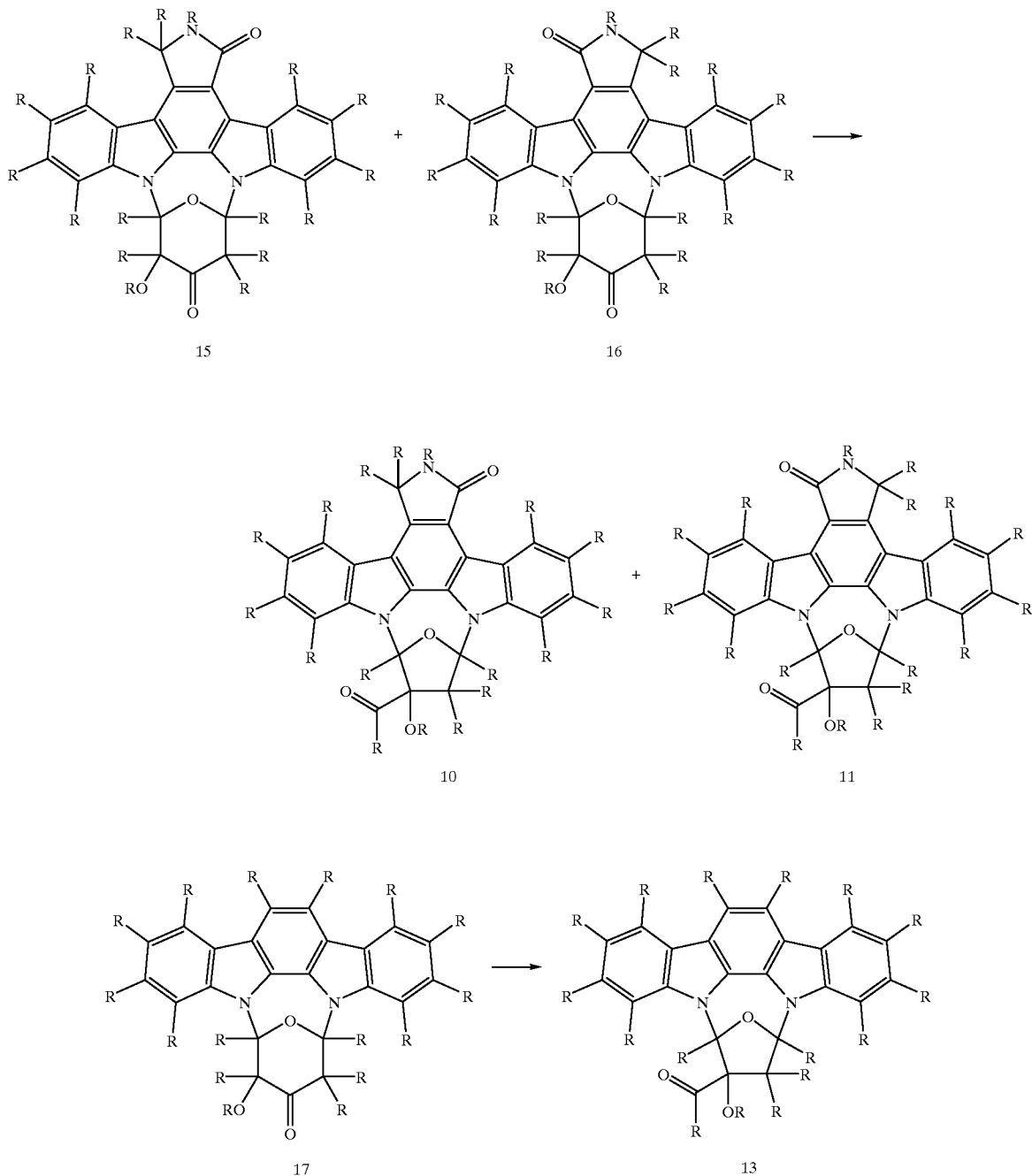

(R represents a substituent comprised of any number and combination of the elements H, C, N, S, Si, O, Cl, Br, I, F)

The invention correspondingly provides a process for the ring expansion of furanosylated indolocarbazoles of structure 10 and/or 11 to the pyranosylated congeners of structure 15 and/or 16 illustrated in Scheme VII below (Ootsuka et al.). A preferred embodiment employs, but is not limited to, a multistep procedure wherein 10 and/or 11 is first reduced with LiBH$_4$ and then the derived diol is oxidized. The resulting intermediate compound is then subjected to a Bronsted or a Lewis acid such as camphor sulfonic acid (CSA), para-toluene sulfonic acid (PTSA), or BF$_3$.Et$_2$O to promote ring expansion. BF$_3$.Et$_2$O is used in some preferred embodiments.

Scheme VII
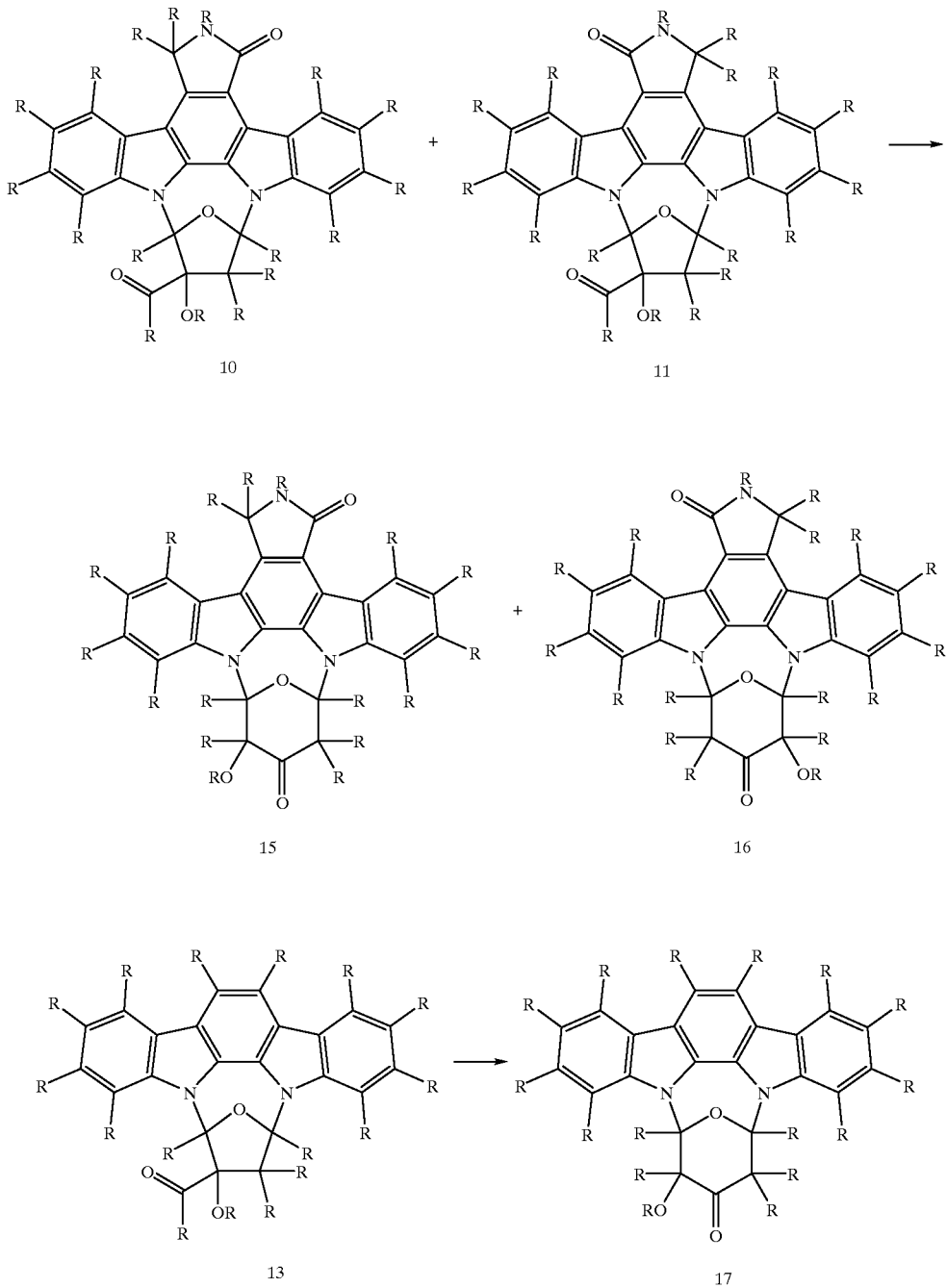
(R represents a substituent comprised of any number and combination of the elements H, C, N, S, Si, O, Cl, Br, I, F)
It is an advantage of the invention that the combined processes provide efficient access to useful indolocarbazoles such as (+)- and (−)-K252a, (+)- and (−)-RK-286c, (+)- and (−)-MLR-52, (+)- and (−)-staurosporine, and the like depicted below.

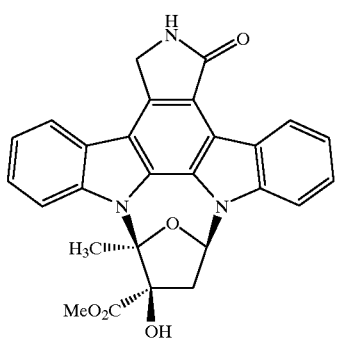
(+)-K252a
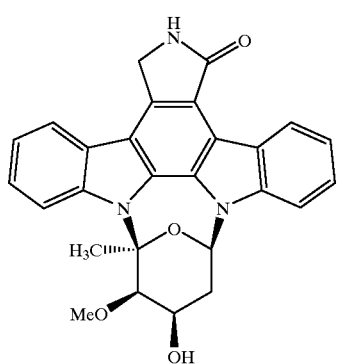
(+)-RK286c
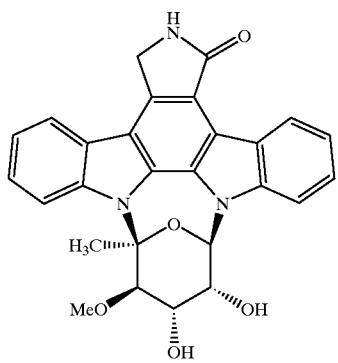
(+)-MLR-52
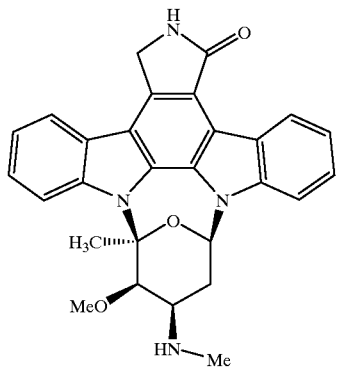
(+)-Straurosporine
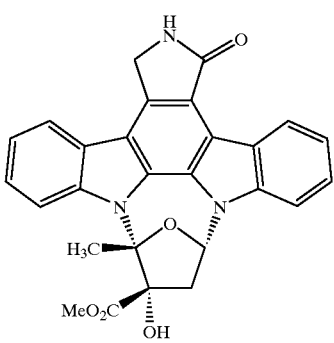
(−)-K252a
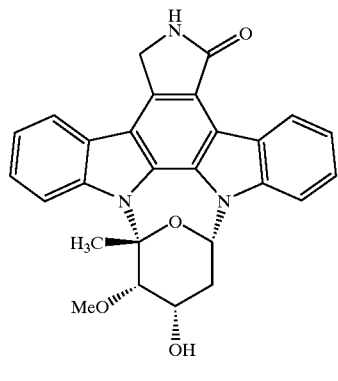
(−)-RK286c
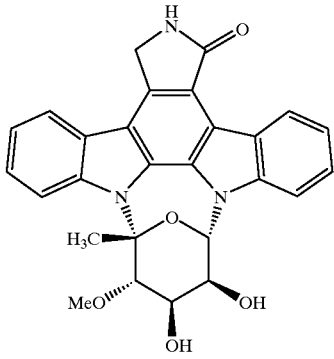
(−)-MLR-52
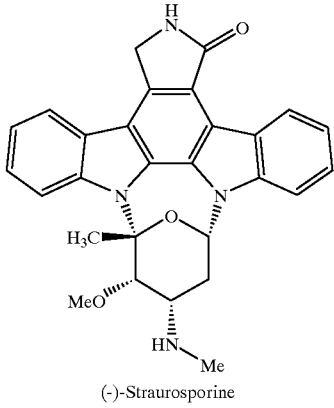
(−)-Straurosporine

EXAMPLES

The following are presented to further illustrate and explain the present invention and should not be taken as limiting in any regard. Unless otherwise indicated, all parts and percentages are by weight and are based on the weight of the components at the indicated stage of processing. Rotations on indolocarbazole were obtained on methanol solutions. Compound structural assignments were in accord with infrared and high-field $^1$H (500 MHz) and $^{13}$C (125 or 62.5 MHz) NMR spectra, as well as appropriate parent identification by high-resolution mass spectrometry.

Example 1

Enantioselective Preparation of Tertiary Alcohols

This example describes a novel rhodium-catalyzed C—C bond forming reaction that allows asymmetric access to 21 (95% ee) and 22 (93% ee) in only two and three steps from methyl acetoacetate (18) (Scheme VIII). In this scenario α-keto ester 21 was produced from the rhodium-catalyzed decomposition of 19 in the presence of S-(+)-1-buten-3-ol (20) (Wood et al.). In the event, complete consumption of 19 was observed after only 20 minutes to reflux in benzene. Proton NMR analysis of the crude reaction indicated the clean formation of a product similar to 19; however, the characteristic methyl ketone singlet had shifted from 2.2 to 1.5 ppm. Clearly the allyloxy or allyloxonium ylide intermediate had undergone [3,3] sigmatropic rearrangement to alcohol (+)-21 (66% yield) (Pirrung et al.). Completion of the tandem rearrangement protocol was achieved by exposing (+)-21 to BF$_3$.Et$_2$O which promoted a clean [1,2]-allyl migration to furnish (−)-22 in 74% yield. In subsequent studies, improved yields were obtained by conducting the tandem rearrangement in one pot. Thus, introducing an equivalent of BF$_3$.Et$_2$O into the cooled [3,3] reaction allows isolation of (−)-22 in an overall yield of 75%.

With an approach firmly established, a chemical correlation study was initiated to confirm both the sense and degree of asymmetric induction for the tandem rearrangement. Analysis of the purified products from both the [3,3] (i.e., (+)-21) and [1,2] (i.e., (−)-22) rearrangements via proton NMR in the presence of Eu(hfc)$_4$ gave the first indication that each step was proceeding with a high degree of stereoselectivity. Conversion of (+)-21 to 23 as outlined in Scheme IX, followed by comparison of the derived bis Mosher ester (24) to samples prepared from S-(+)- and R-(−)-citramalic acid, established that S-(+)-20 (98% ee) had furnished R-(+)-21 (95% ee). Stereoselectivity in the [1,2] shift was established by degradation of (−)-22 to R-(−)-25 followed by DIBAL reduction and proton NMR analysis of the corresponding bis Mosher ester. While the Mosher ester analysis established an ee of 92%, the observation of R-(−)-25 in the degradation proved the absolute stereochemistry in 22 as S.

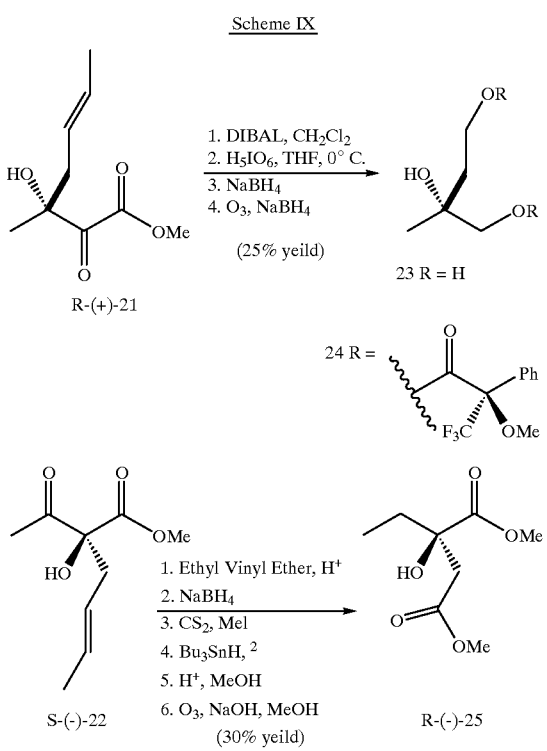

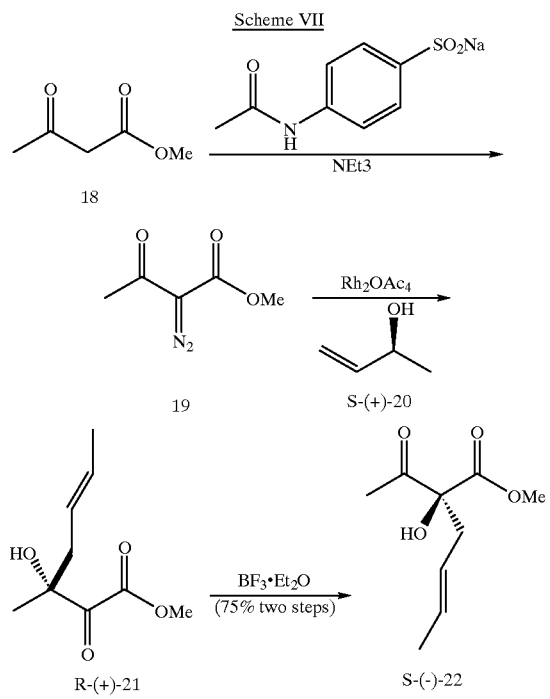

Having established the degree and sense of asymmetric induction the asymmetric synthesis of the requisite acetals 26 and 27 was begun. Thus, reductive ozonolysis of 22 followed by acetal formation provided a ternary mixture. Spectral identification of the isolated products indicated the presence of methyl ketone 26 and furanoses (+)-27a and (+)-27b (Scheme X).

Scheme X

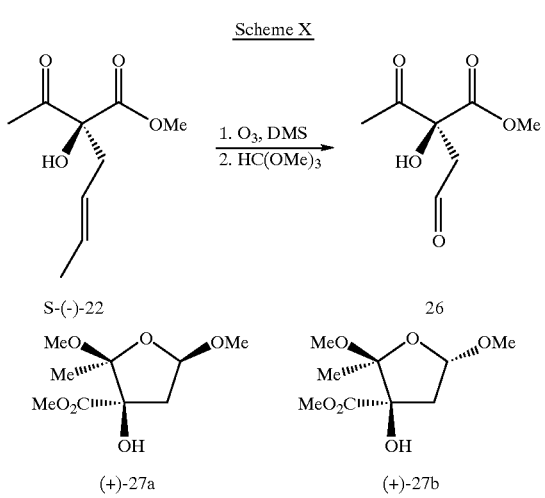

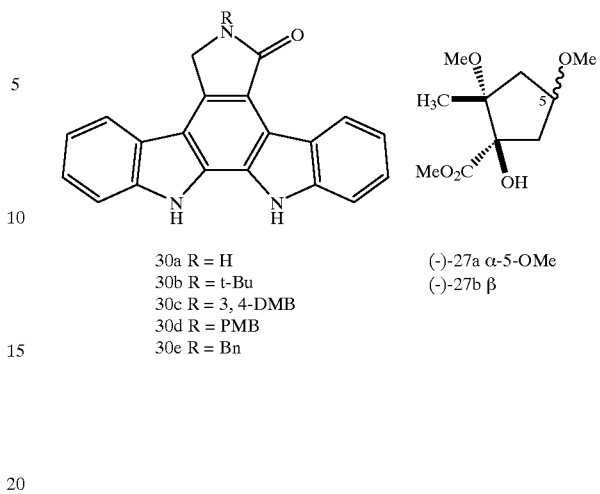

30a R = H
30b R = t-Bu
30c R = 3, 4-DMB
30d R = PMB
30e R = Bn (-)-27a α-5-OMe
(-)-27b β

Example 2

Preparation and Furanosylation of Indolocarbazoles

The Synthesis of K252a

This example describes the coupling of diazolactams 28 and 2,2'-biindole 29 to produce an intermediate that undergoes cycloaromatization to furnish the indolocarbazoles 30. Application of this strategy allows efficient access to both the parent aglycone (30a) and the selectively protected derivatives (30b–c). Of the latter, 30c is employed in the total synthesis of K252a. Overall, preparation of the enantioenriched furanoses 27 (described in Example 1 above) and aglycon unit 30c and their conversion to 14 require only eleven synthetic operations with a longest linear sequence of seven steps.

Scheme XI

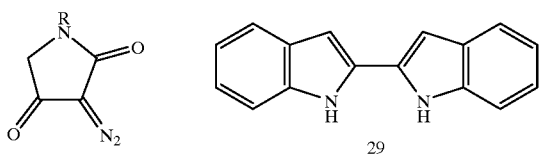

28a R = H
28b R = t-Bu
28c R = 3, 4-DMB
28d R = PMB
28e R = Bn

The feasibility of the carbenoid approach to 30 was initially assessed by reaction of 28a (1.0 equiv) with indole (3.0 equiv) in the presence of catalytic $Rh_2(OAc)_4$ (0.01 equiv, Scheme XII). After only 12 h, TLC analysis indicated complete consumption of 28a and standard work-up and isolation procedures furnished 31 in 65% yield. Similar conditions proved ineffective for the coupling of 28a with 29, and it was only after considerable experimentation that a procedure was developed which provided satisfactory yields of 30a. The use of degassed pinacolone proved critical as this solvent was found to be both compatible with the carbenoid chemistry and capable of solvating the diindole substrate. Under these conditions the coupling of 28a and 29 proceeded directly to 30a (K252c) in 25% yield. Presumed intermediates 32 and 33 were not apparent by TLC or NMR analysis of the crude reaction mixture. In an attempt to complete the synthesis, the cycloglycosidation of 27 with 30a revealed a tendency of the latter to alkylate at the amide nitrogen; thus, selectively protected aglycones 30b–e. were employed. Preparation of the corresponding diazolactams 28b–e, followed by reaction with 29 in the presence of $Rh_2(OAc)_4$ (0.1 equiv) established that several protecting groups can withstand the carbenoid conditions and that the best yields (50–62%) are obtained within the benzyl class (e.g., 28c,d,e⊘30c,d,e Scheme XII). To provide the most flexibility in the eventual deprotection 3,4-dimethoxybenzyl protected aglycone 28c was employed.

Scheme XII

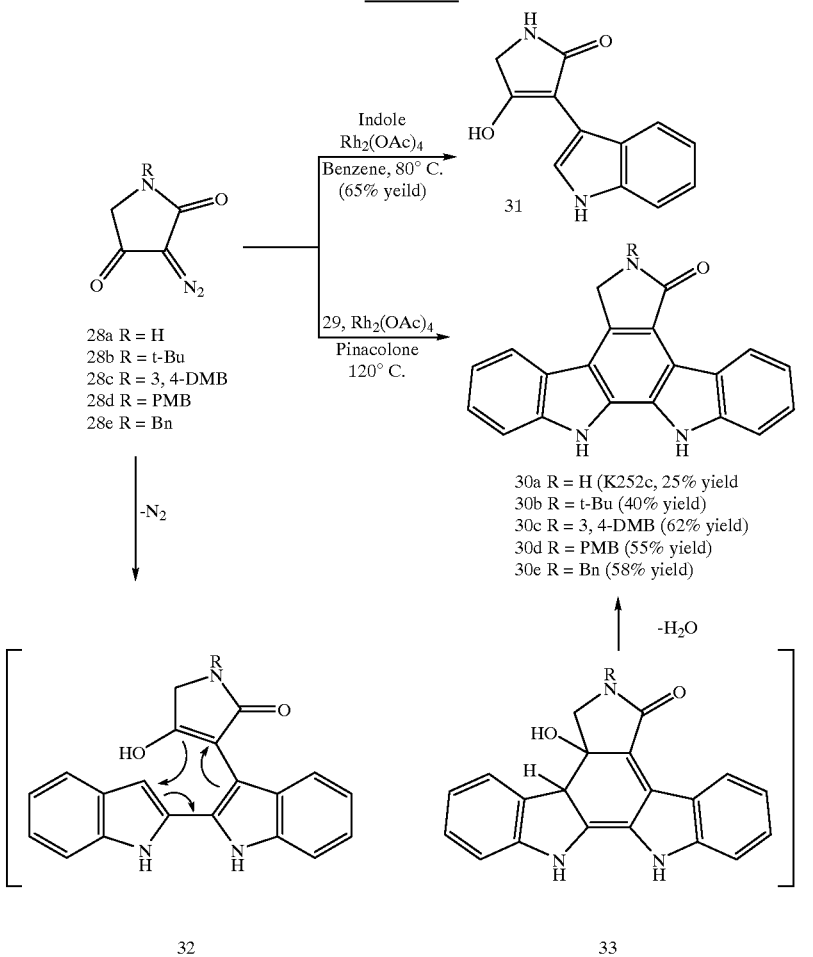

Having gained efficient access to 30c, attention was turned to the preparation of the furanose components (27). To this end, a novel tandem rearrangement protocol was developed that combines methyl 2-diazo-3-oxobutyrate (19) and S-(+)-1-buten-3-ol (20) to furnish (−)-22 in a single-pot (92% ee, 75% yield). Reductive ozonolysis of (−)-22 followed by acid promoted cyclization in methanol produced (+)-27a and (+)-27b in good yield.

Scheme XIII

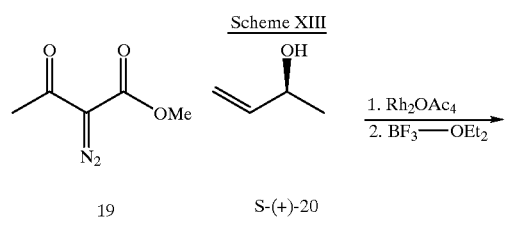

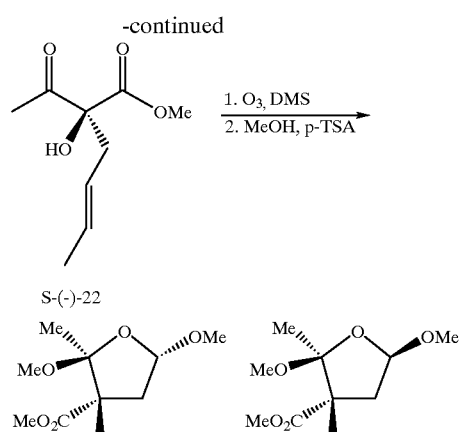

With both (+)-27 and 30c in hand the cycloglycosidative coupling was investigated. Of several conditions reported by McCombie, et al., for related transformations, camphorsulfonic acid in 1,2-dicbloroethane was found to be the catalyst and solvent of choice. In the event, 30c and (+)-27a and 27b combined rapidly to form two regioisomeric pairs of open chain monoamino acetal diastereomers (34 and 35). Prolonged heating of the quaternary mixture induced cycloglycosidation to only two of the four possible diastereomers.

Scheme XIV

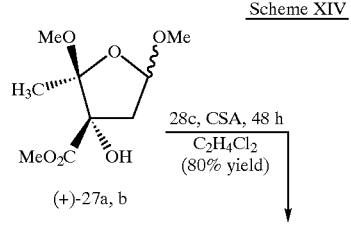

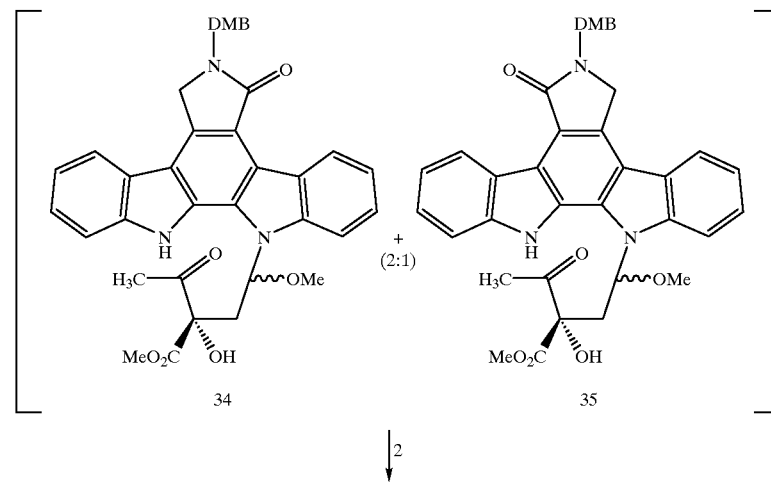

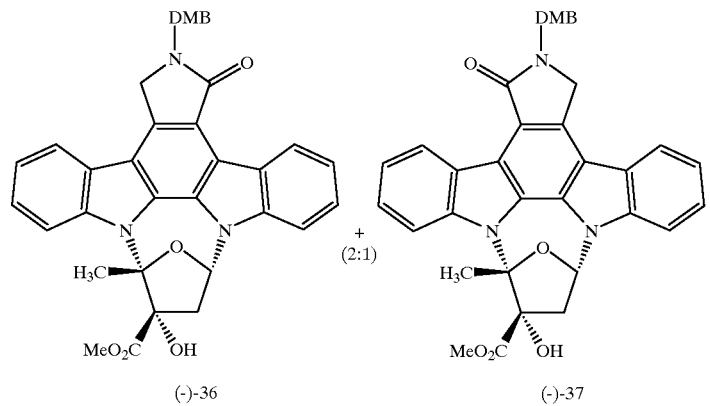

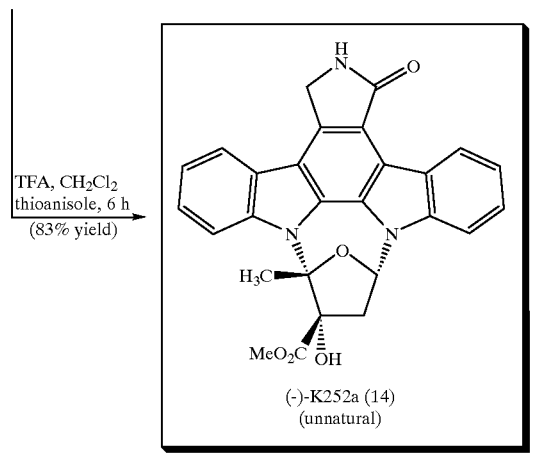

(-)-K252a (14)
(unnatural)

TFA, CH₂Cl₂
thioanisole, 6 h
(83% yield)

Preliminary assignment of structure was based on $^1$H NMR analysis which indicated that the reaction had produced the regioisomeric products (−)-36 (55% yield) and (−)-37 (25% yield). The observed formation of (−)-14 upon deprotection of (−)-36 under standard conditions (TFA/CH₂Cl₂/thioanisole) established the cycloglycosidation as both regio- and stereoselective for the natural configuration. Comparison of synthetic (−)-14 to material derived from natural sources established its identity as the unnatural enantiomer of K252a.

Total synthesis of the natural enantiomer (i.e., (+)-14) was effected in an analogous fashion using 28c and (−)-27a and (−)-27b as coupling partners (Scheme XV). The latter compound was prepared via the tandem [3,3]/[1,2] rearrangement protocol (described in Example 1 above) using R-(−)-1-nonen-3-ol (38) as the source of asymmetry.

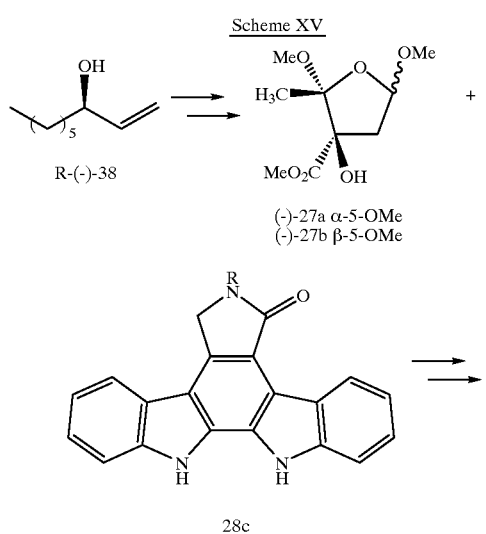

Scheme XV

R-(−)-38

(−)-27a α-5-OMe
(−)-27b β-5-OMe

28c

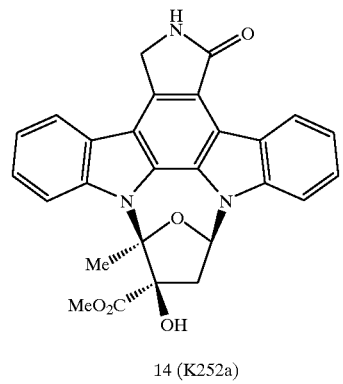

14 (K252a)

In summary, application of a novel carbenoid mediated synthesis of K252c coupled with a highly selective tandem (3,3)/(1,2) rearrangement protocol provides efficient access to both (+)- and (−)-K252a.

Example 3

Furanosylation of Alternative Indolocarbazoles and the Interconversion of Furanosylated and Pyranosylated Indolocarbazoles This example reports results wherein an indolocarbazole simpler than that described Example 2 is subjected to furanosylation. The derived product 40 is further manipulated into a ring-expansion substrate 41 or 42 that undergoes conversion to the corresponding pyranosylated indolocarbazole 43 or 44, respectively (Stoltz et al. 1995). It is further demonstrated in this example that the α-hydroxy ketone congener 43 undergoes facile oxidative ring contraction to the furanosylated indolocarbazole upon exposure to CuCl in methanol (Stoltz et al. 1996).

For the furanosylation, indolo [2,3-a]carbazole (39) was coupled with 27a and 27b in a manner similar to that employed in the synthesis of K252a desribed in Example 2. This coupling again proved highly stereoselective and produced 40 as the only isolable product in 85% yield.

Scheme XVI

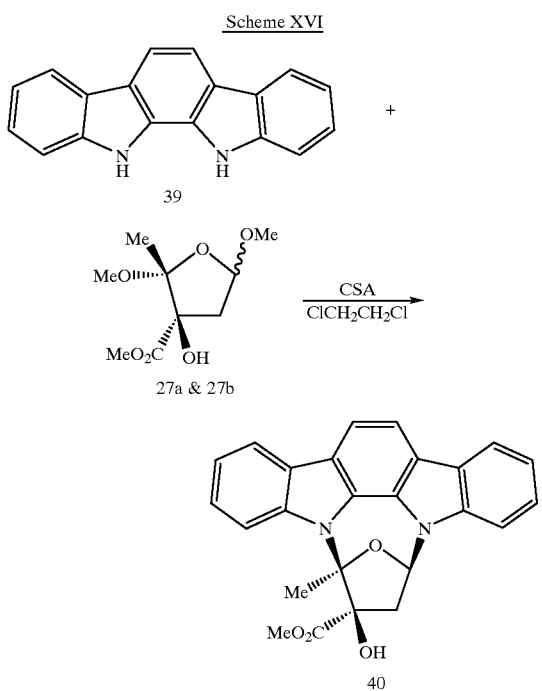

Turning to the ring expansion, it was soon discovered that transformation of 40 into aldehyde 41 followed by treatment with $BF_3.Et_2O$ results in a regio- and stereoselective rearrangement to the pyranosylated indolocarbazole 43. At this stage all that remained for the preparation of 44 was what appeared to be a trivial alkylation of the C(3') hydroxyl. Ketone 43 surprisingly proved quite resistant to methylation under numerous alkylation conditions. In addition, attempts to incorporate directly the methyl substituent by promoting the rearrangement with a source of Me+ (e.g., Meerweinis reagent, TMSOTf/TMSOMe, and MeOTf) also failed. Eventually, these difficulties led to the development of an alternative strategy that targeted dimethyl acetal 42 as the substrate for a ring expansion (Scheme XVII). Although 42 was readily produced under a variety of conditions, its instability to chromatographic purification required the employment of montmorillonite clay K-10 to promote acetal formation. Removal of the clay via filtration, solvent exchange with $Et_2O$, and subsequent treatment with $BF_3.Et_2O$ resulted in the slow (72 h, 25° C.) conversion of 42 to 44 (50% yield).

Scheme XVII

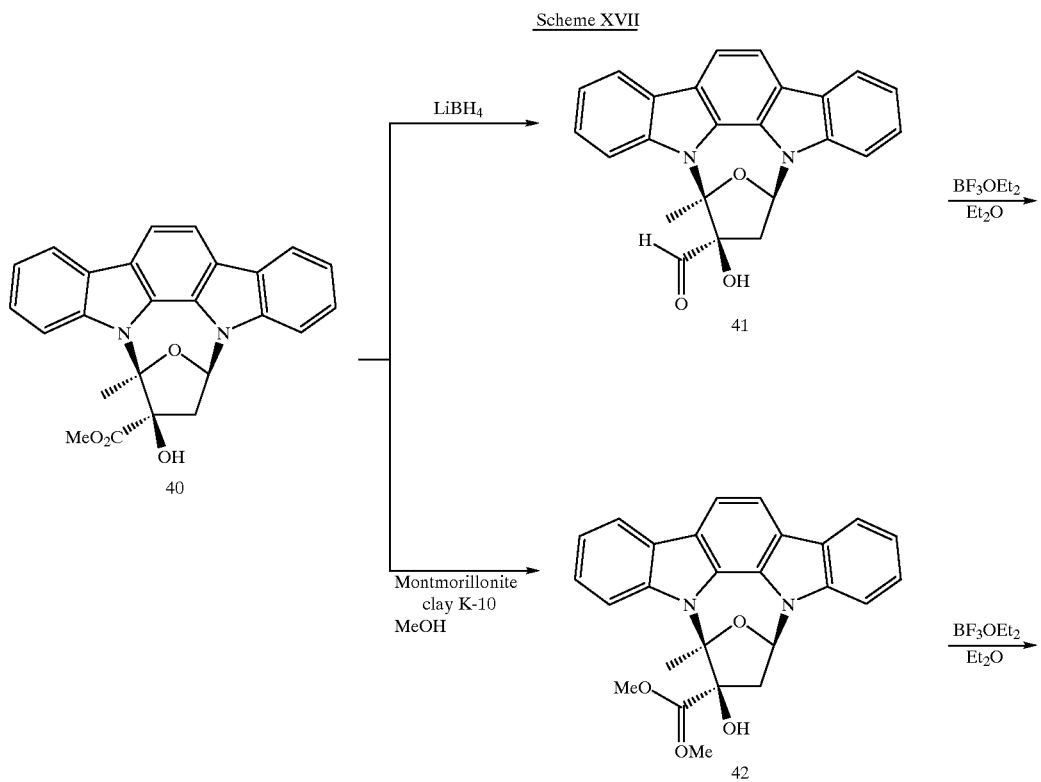

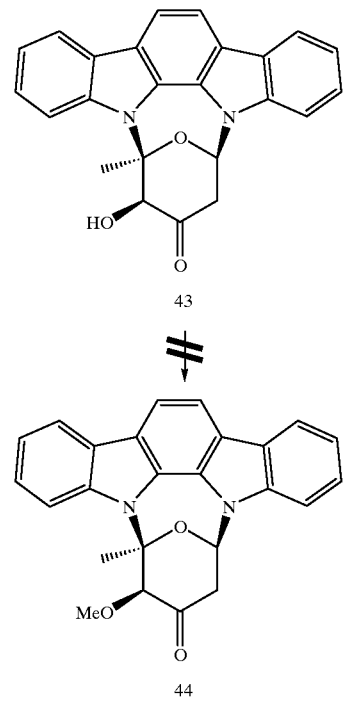

Having rapidly assembled α-methoxy ketone 44, its conversion to the desamido pyranosylated indolocarbazoles was investigated. To this end, the analogs of RK-286c (46) and TAN-1030a (47) were readily prepared from 44 under standard conditions using NaBH$_4$ and H$_2$NOH.HCl, respectively (Scheme XVIII).

While the above model investigations established the feasibility of a regio and stereoselective ring expansion, subsequent attempts to alkylate the derived α-hydroxy ketone 43 proved problematic. Of note is the propensity of 43 to undergo loss of the indolocarbazole nucleus as evidenced by isolation of 39 as the major product in many of Scheme XVIII

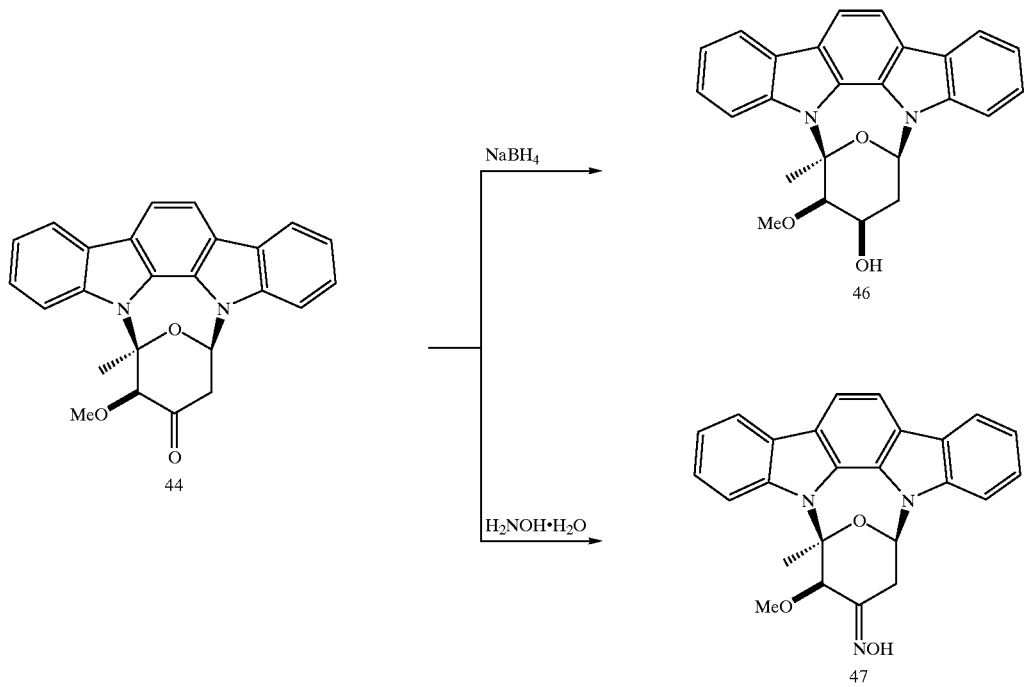

the alkylation attempts. In an effort to avoid this deleterious event attention was turned to methylation procedures that appeared to proceed under essentially neutral conditions. While these efforts failed to produce any of the desired α-methoxy ketone 44, the conditions comprising CuCl and DCC in MeOH were observed to cleanly convert 43 to 40, the functionalized K252a sugar moiety. Apparently these conditions induced either ring contractive α-ketol rearrangement and oxidation (i.e., 43→41→40) or oxidation and ring contractive "benzilic" acid rearrangement (i.e., 43→48→40). While not wishing to be bound to any theory, since oc-hydroxy aldehyde 41 failed to undergo conversion to 40 under identical conditions, the latter of these two mechanistic possibilities appears most likely. In addition, subsequent investigations have revealed CuCl in MeOH without added DCC to be the optimal conditions for converting 43 to 40 (95% yield).

Example 4

The Synthesis of Staurosporine, RK-286c, MLR-52, and K252a

This example demonstrates that the tertiary alcohol and indolocarbazole syntheses, the indolocarbazole furanosylation, and the ring-expansion protocol described in the above Examples can be used to prepare pyranosylated indolocarbazoles that are suited for conversion to staurosporine (49) RK-286c (50), MLR-52 (51), and K252a (14) (Link et al.).

The synthesis of 49-51 began by converting the K252a precursor (36, described above in Example 2) to the corresponding aldehyde via LiBH$_4$ reduction and then Moffatt oxidation (63% yield overall, Scheme XX). Guided by the α-ketol rearrangement results described above, 50 was exposed to BF$_3$.Et$_2$O and the reaction allowed to stir at room temperature for 3 h. Given that the proposed ring-expansion

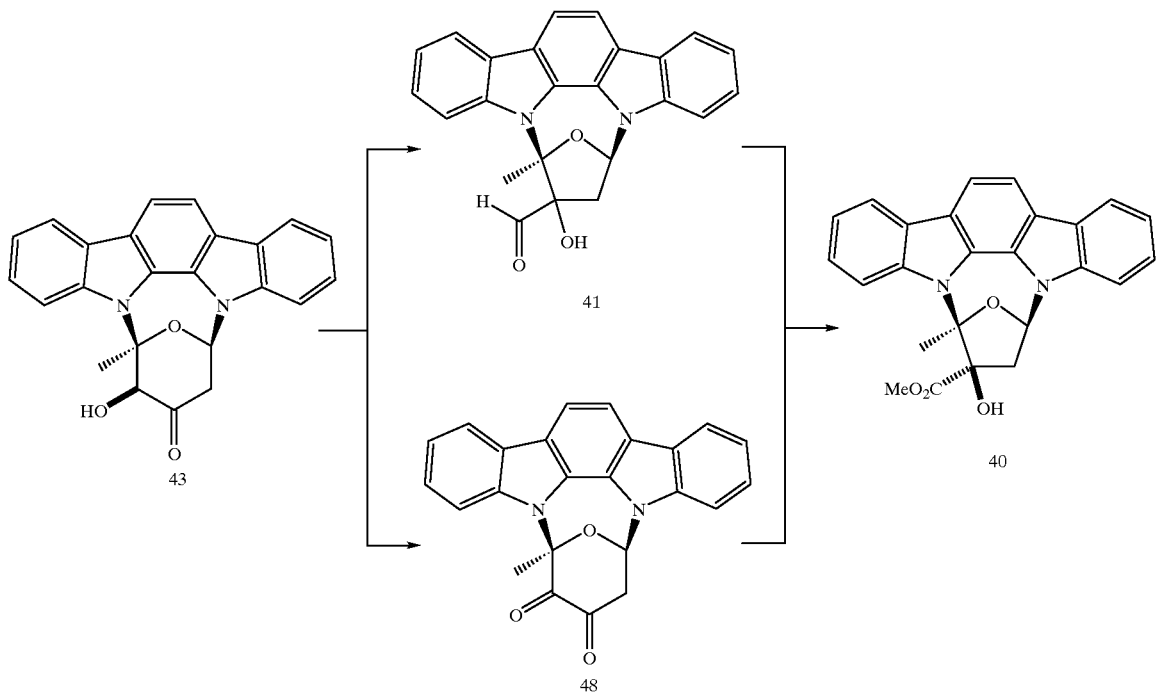

Scheme XIX of 50 to 51 could proceed to a mixture of regio- and stereoisomeric products, treatment of (+)-50 with BF$_3$.OEt$_2$ in Et$_2$O (2.2 equiv, 25–30° C., 24 h) surprisingly produces a single product, (+)-51, in 85% yield. The regio- and stereochemical outcome of this reaction, which were confirmed by spectral comparison to a closely related model and the conversion of (+)-51 to (+)-50 (vide infra).

Scheme XX

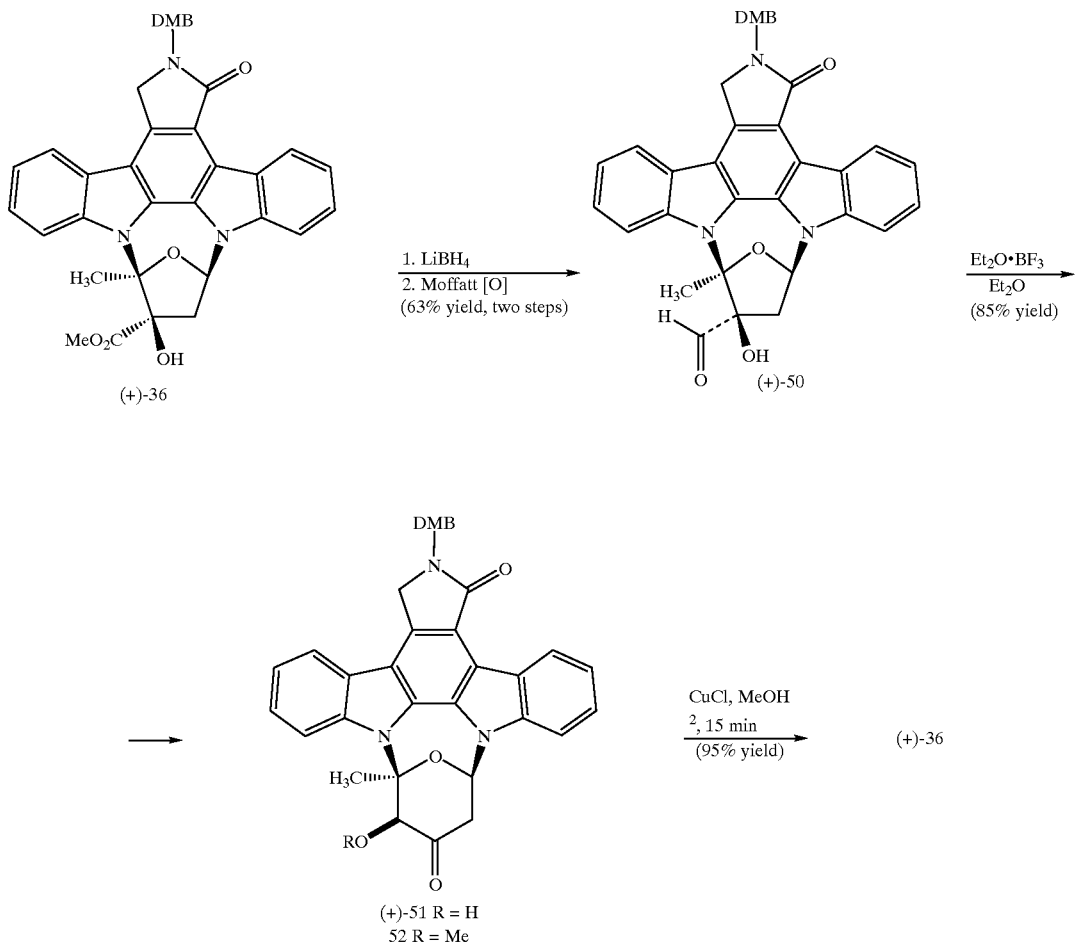

As expected from the data presented in Example 3, attempts to methylate 51 were unproductive and again led to the observation that exposure of (+)-51 to CuCl in MeOH results in a highly stereoselective oxidation/ring-contraction sequence that produces (+)-36 in 95% yield.

Turning from the potentially biomimetic synthesis of (+)-K252a to the synthesis of 49-51, it was discovered that (+)-51 undergoes selective conversion to (+)-54 upon sequential treatment with $NaBH_4$ and NaH/MeI. Having installed all of the functional groups common to (+)-50-51, the approach diverged into the synthesis of (+)-RK286c and (+)-MLR-52. The former was completed via deprotection of (+)-54 (TFA/anisole) while the latter required a three-step sequence that was initiated by exposing (+)-54 to Martin's sulfurane. Oxidation of the derived olefin with $OsO_4$ followed by deprotection of the resultant diol (+)-55 produced (+)-51 (Scheme XXI).

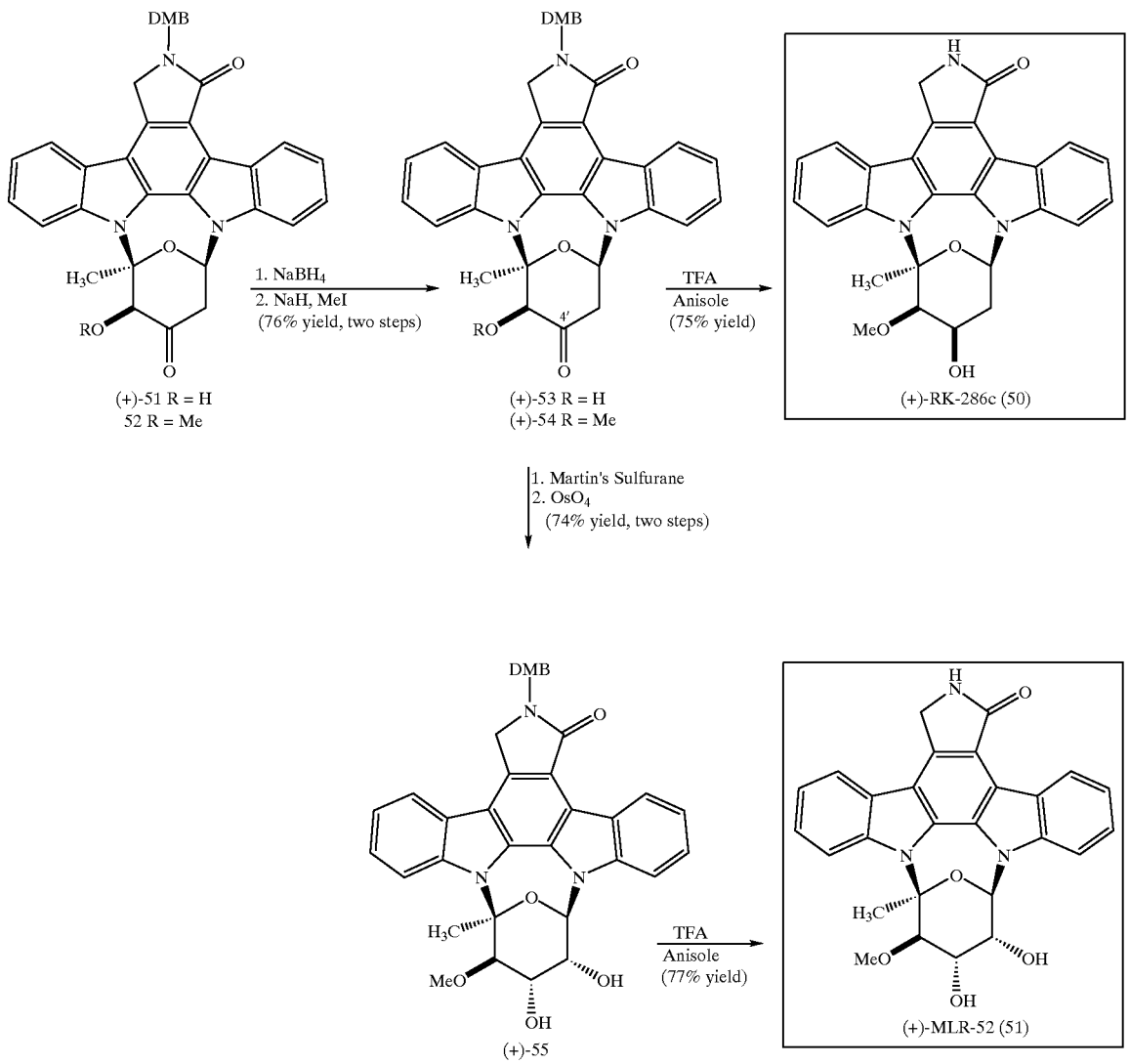

Scheme XXI

The inability to prepare a-methoxy ketone 52 guided an approach to staurosporine along a route wherein the 4' nitrogen is introduced via conversion of (+)-51 to the corresponding oxime (−)-56 (H$_2$NOH.HCl, NaOAc, Scheme XXII). Crucial for the success of this approach is the fact that (−)-56, unlike ketone (+)-51, readily undergoes alkylation to the C(3') methyl ether (MeI, KOH, n-Bu$_4$NBr). Stereoselective reduction of the derived methoxy oxime (−)-57 (H$_2$, PtO$_2$) to the corresponding primary amine ((+)-58) followed by monomethylation (HCO$_2$COCH$_3$, BH$_3$.DMS) and deprotection (TFA) produced (+)-staurosporine (49).

Scheme XXII

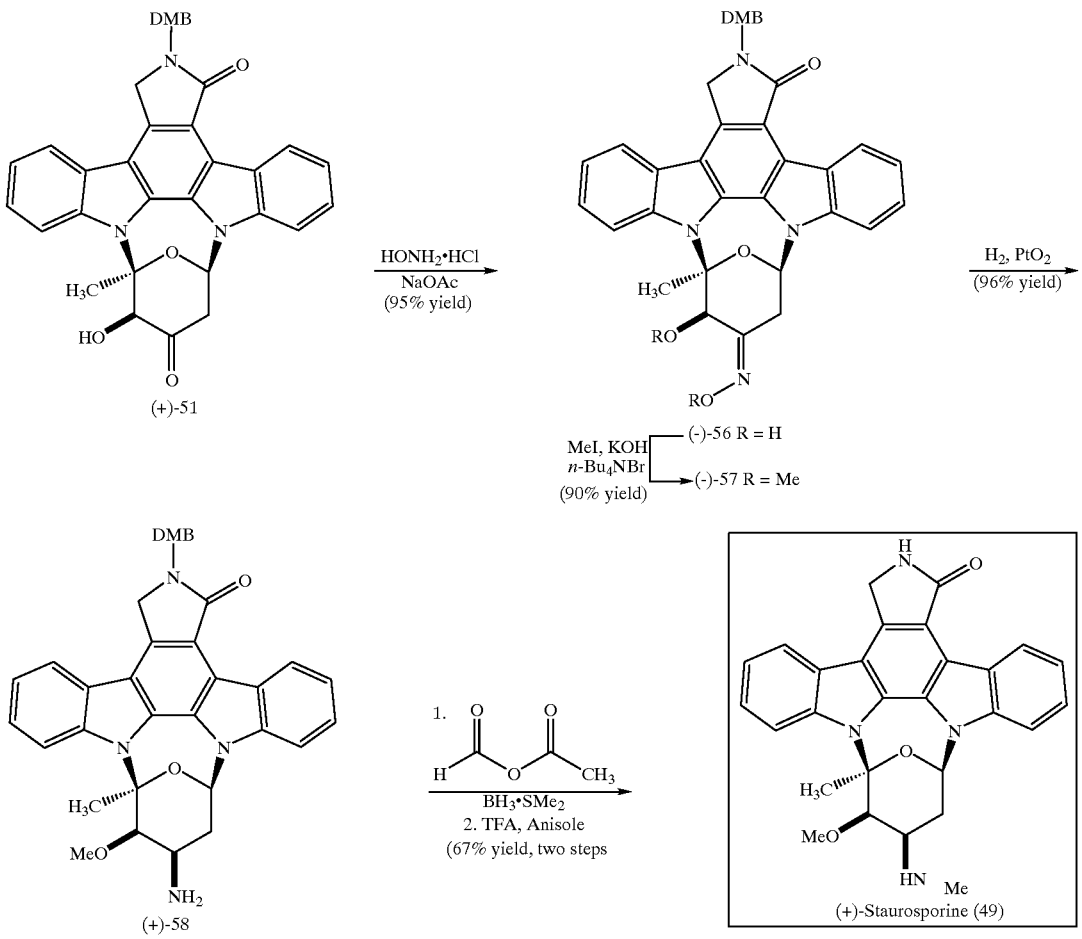

In summary, efforts to devise an efficient synthesis of the pyranosylated indolocarbazoles via a common intermediate [i.e., (+)-36] were successful in delivering (+)-49 (19 steps), (+)-50 (17 steps), and (+)-51 (19 steps). In addition, these investigations have revealed both ring-expansion and -contraction reactivity that may play a central role in the biogenesis of both the furanosylated and pyranosylated members of this important class of natural products.

Experimental procedures for selected compounds in Examples 1 to 4 may be found in international publication number WO 97/07081 to Yale University and Wood, et al., Feb. 27, 1997, filed as PCT/IB96/00987 on Aug. 9, 1996, claiming priority benefit of U.S. application Ser. No. 60/002,164, filed Aug. 11, 1995, which is incorporated by reference.

REFERENCES

Fredenhagen, A.; Peter, H. H. *Tetrahedron* 52: 1235 (1996).
Link, J. T., et al., *J. Am. Chem. Soc.* 115: 3782 (1993).
Ootsuka, Y. et al. . Jpn. Kokai Tokkyo Koho JP05247054, (1993).
Omura, S. et al. *J. Antibiotics* 48: 525 (1995).
McCombie, S. W., et al., *Bioorg. Med. Chem. Lett.* 3: 1537 (1993).
Pirrung, M. C., et al., *J. Org. Chem.* 60: 2112 (1995).
Stolz, B. M., and Wood, J. L., *Tetrahedron Lett.* 36: 8543–8544 (1995).
Stoltz, B. M., and Wood, J. L., *Tetrahedron Lett.* 37: 3929–3930 (1996).
Wood, J. L., et al., *J. Amer. Chem. Soc.* 117: 10413–10414 (1995).
Wood, J. L., et al., *J. Amer. Chem. Soc.* 118: 10656–10657 (1996).
Wood, J. L., et al., *Tetrahedron Lett.* 37: 7335–7336 (1996).

All the references cited herein are expressly incorporated herein by reference. The invention was made with partial government support under American Cancer Society grant JFRA-523. The government has certain rights in the invention.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

We claim:

1. A process for the stereoselective preparation of pyranosylated indolocarbazoles of the formula by ring expansion of the corresponding furanosylated indolocarbazole of the formula

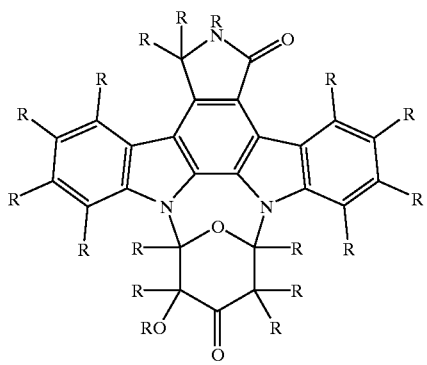

in the presence of a Bronsted acid or a Lewis acid, wherein R is selected from the group consisting of a) a $C_{3-10}$ branched or unbranched alkyl, optionally partially or fully halogenated, hydroxy, $C_{1-3}$ alkyloxy, amino, alkylamino, b) an aryl optionally substituted with one to five groups consisting of halo, hydroxy, $C_{1-3}$ alkyloxy;

c) a hydrogen;

d) a halogen; and e) mixtures of any of these.

2. A process according to claim 1 wherein the ring expansion is carried out in the presence of a Lewis acid.

3. A process according to claim 1 wherein the ring expansion is carried out in the presence of camphor sulfonic acid, para-toluene sulfonic acid or to $BF_3.Et_2O$.

4. A process according to claim 3 wherein the ring expansion is carried out in the presence of camphor sulfonic acid.

5. A process according to claim 3 wherein the ring expansion is carried out in the presence of $BF_3.Et_2O$.

6. A process according to claim 1 wherein the ring expansion is carried out in a multistep procedure wherein a compound of the formula

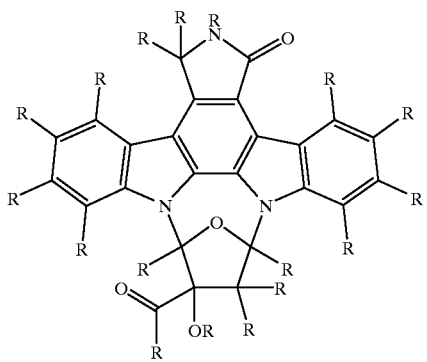

is first reduced with $LiBH_4$, the derived diol is oxidized, and the resulting intermediate compound is then subjected to $BF_3.Et_2O$.

7. A process according to claim 1 wherein R is H, Bn or a halogen.

8. A process according to claim 7 wherein R is H, Me or Bu.

9. A process according to claim 1 wherein R is selected from the group consisting of H, Me, t-Bu, 3,4-DMB, and PMB.

10. A process according to claim 1 wherein the pyranosylated indolocarbazole prepared is staurosporine.

11. A process according to claim 1 wherein the pyranosylated indolocarbazole prepared is RK286c or MLR-52.

12. A process for converting a glycosylated reactant of the formula

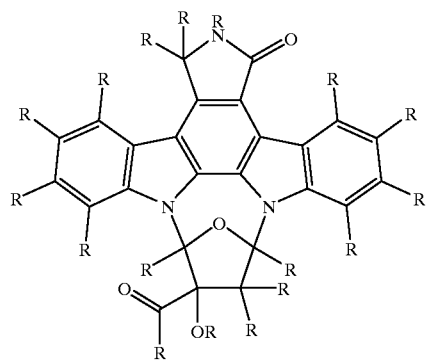

wherein R represents an H, a halogen, Me, Bu, Bn, OMe, DMB, PMB, NHMe, $NH_2$ or OH, comprising subjecting the furanosylated derivative to ring expansion in the presence of a Lewis acid or a Bronsted acid to produce a product of the formula

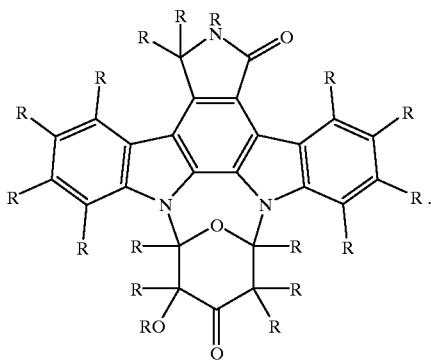

13. A process according to claim 12 wherein the ring expansion is carried out in the presence of camphor sulfonic acid, para-toluene sulfonic acid, or $BF_3.Et_2O$.

14. A process according to claim 12 wherein R is H, a halogen, Me, Bu, OH, OMe or Bn.

15. A process according to claim 13 whrein R is selected from the group consisting of H, Me, t-Bu, 3,4-DMB, and PMB.

16. A process for preparing a compound selected from the group consisting of (+)-staurosporine, (−)-staurosporine, (+)-RK286c, (−)-RK286c, (+)-MLR52, (−)-MLR52, (+)-TAN 1030a, and (−)-TAN 1030a, comprising subjecting the furanosylated derivative to ring expansion in the presence of a Lewis acid or a Bronsted acid to obtain ring expansion to the corresponding pyranosylated derivative.

17. A process according to claim 16 wherein the ring expansion is carried out in the presence of camphor sulfonic acid, para-toluene sulfonic acid, or $BF_3.Et_2O$.

18. A process according to claim 16 wherein the compound prepared is (+)- or (−)-staurosporine.

19. A process according to claim 16 wherein the compound prepared is (+)-RK286c, (−)-RK286c, (+)-MLR52, or (−)-MLR52.

20. A process according to claim 19 wherein the ring expansion is carried out in the presence of camphor sulfonic acid, para-toluene sulfonic acid, or $BF_3.Et_2O$.

21. A process for the preparation of a pyranosylated indolocarbazole which comprises conducting a ring expansion of the corresponding furanosylated indolocarbazole in the presence of a Bronsted acid or a Lewis acid.

22. A process according to claim 21 wherein the ring expansion is carried out in the presence of camphor sulfonic acid, para-toluene sulfonic acid or $BF_3.Et_2O$.

* * * * *